United States Patent
Stone et al.

(10) Patent No.: US 7,323,012 B1
(45) Date of Patent: Jan. 29, 2008

(54) ANKLE IMPLANT

(75) Inventors: Kevin T Stone, Winona Lake, IN (US);
Brian K Berelsman, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 679 days.

(21) Appl. No.: 10/802,679

(22) Filed: Mar. 17, 2004

(51) Int. Cl.
*A61F 2/42* (2006.01)

(52) U.S. Cl. .................................. 623/21.18

(58) Field of Classification Search ............ 623/16.11, 623/18.11, 21.11, 21.18
See application file for complete search history.

(56) References Cited

U.S. PATENT DOCUMENTS

| 3,839,742 | A | * | 10/1974 | Link ....................... 623/21.18 |
| 3,872,519 | A | | 3/1975 | Giannestras et al. |
| 4,470,158 | A | * | 9/1984 | Pappas et al. ............ 623/20.21 |
| 5,326,365 | A | | 7/1994 | Alvine |
| 5,658,338 | A | * | 8/1997 | Tullos et al. ............. 623/22.39 |
| 5,766,259 | A | | 6/1998 | Sammarco |
| 5,824,106 | A | | 10/1998 | Fournol |
| 6,183,519 | B1 | | 2/2001 | Bonnin et al. |
| 6,409,767 | B1 | * | 6/2002 | Perice et al. ............. 623/21.18 |
| 7,011,687 | B2 | * | 3/2006 | Deffenbaugh et al. ... 623/21.18 |
| 2004/0002768 | A1 | | 1/2004 | Parks et al. |

FOREIGN PATENT DOCUMENTS

WO    WO 91/07931    * 6/1991

* cited by examiner

*Primary Examiner*—Anuradha Ramana
(74) *Attorney, Agent, or Firm*—Harness, Dickey & Pierce, P.L.C.

(57) ABSTRACT

A modular ankle implant. The implant includes a tibial component coupled to a talar component with a bearing. The bearing is adapted for hinged articulation relative to the talar component and limited rotation relative to the tibial component.

24 Claims, 6 Drawing Sheets

US 7,323,012 B1

ANKLE IMPLANT

INTRODUCTION

The ankle has a complex joint that allows several rotational motions of the foot, such as dorsiflexion and plantarflexion in the sagittal plane, inversion and eversion in the coronal plane, and abduction and adduction in the transverse plane. Because of the complexity of the ankle joint, total ankle replacement has not been as successful as hip or knee replacements. The early ankle arthroplasty designs were either constrained or nonconstrained and included cemented components. The constrained designs have inherent stability, but can lead to loosening and infection. The nonconstrained designs can be unstable and can cause impingement, but are less prone to loosening.

Newer designs are semi-constrained, and generally include a tibial component, a talar component and a bearing between the tibial and talar components. The bearing can be mobile allowing rotation and sliding relative to the tibia or can be fixed within the tibial component. While these designs are still under long-term evaluation with conflicting reports of success, improved semi-constrained ankle implants are still desirable.

SUMMARY OF THE INVENTION

The present teachings provide in various embodiments a modular ankle joint implant. The implant includes a tibial component coupled to a talar component with a bearing. The bearing is adapted for hinged articulation relative to the talar component and limited rotation relative to the tibial component.

The present teachings also provide for a bearing that matingly articulates with the talar component. The bearing can have a bearing dome that mates with a tibial dome of the tibial component for relative rotation therebetween. A bearing flange may engage a tibial flange to limit rotation of the bearing relative to the tibial component.

The present teachings also provide a modular ankle implant that has a first component having a first dome, and a second component having a second dome. The first and second domes articulate for relative rotation therebetween in a transverse plane.

The present teachings also provide a method for implanting an ankle joint prosthesis between a tibia and a talus. The method includes attaching a tibial component to the tibia, attaching a talar component to the talus, and articulating a bearing for limited rotation relative to the tibial component and hinged movement relative to the talar component.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

Figure 1:
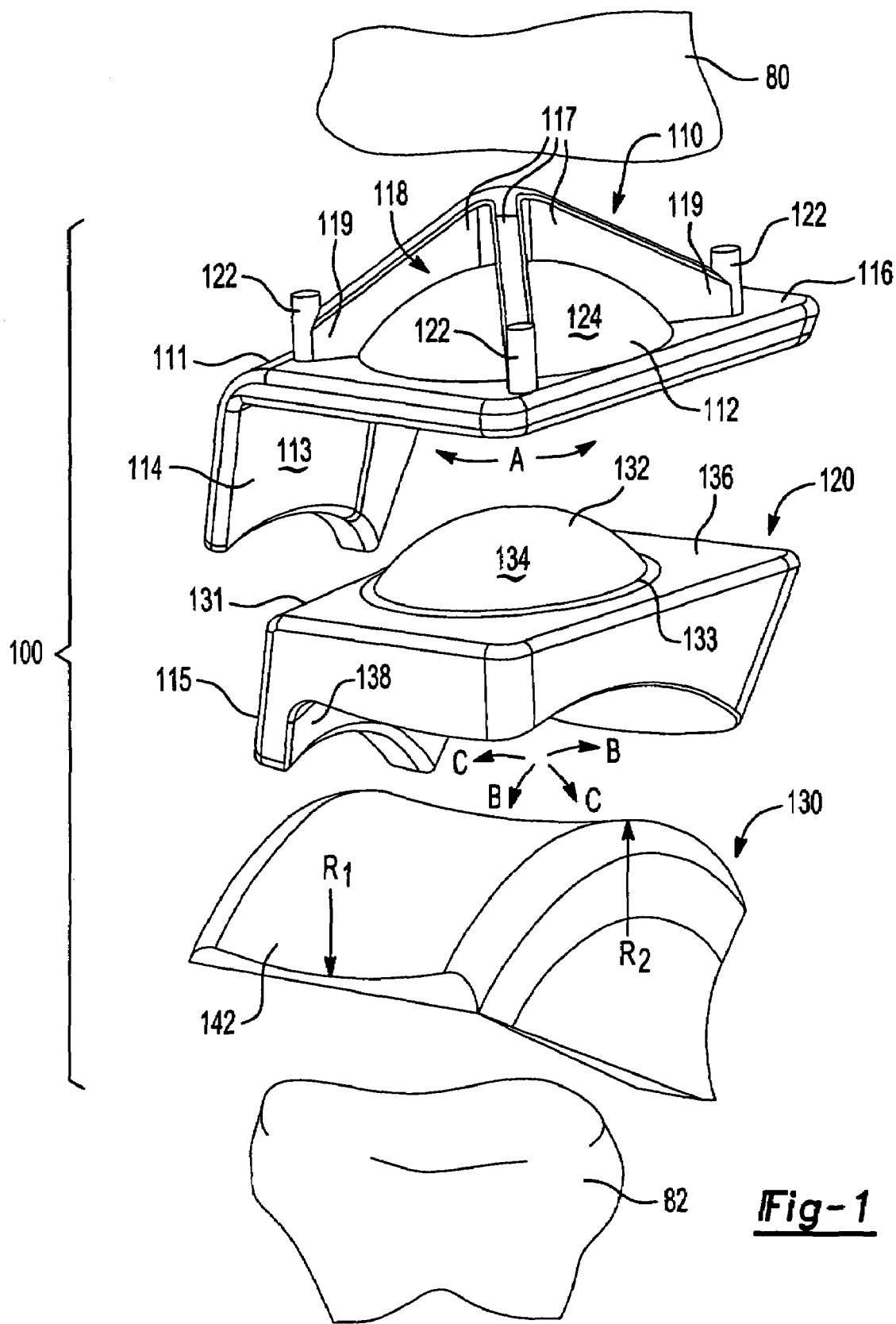
FIGS. 1 and 2 are exploded isometric views of an ankle implant according to the present teachings.

The following description of various embodiments is merely exemplary in nature and is in no way intended to limit the invention, its application, or uses.

Various aspects of an ankle implant 100, 200 according to the present teachings is illustrated in FIGS. 1-5, and 6-9. The ankle implant 100/200 is modular and includes a tibial component 110/210, a bearing 120/220 and a talar component 130/230. The tibial component 110/210 is implanted into the tibia 80 and the talar component 130/230 is implanted into the talus 82. The bearing 120/220 provides hinged articulation with the talar component 130/230, and articulates with the tibial component 110/210 for limited rotation therebetween.

In one aspect and referring to FIGS. 1-5, the tibial component 110 includes an annular tibial plate 116 and a tibial flange 114 that extends from a side 111 of the tibia plate 116 such that the tibial plate 116 and the tibial flange 114 define an L-profile. The tibial plate 116 defines an opening 128 which is capped by a tibial dome 112. In one aspect, the tibial dome 112 includes a convex bone-engaging surface 124 that rises above the tibial plate 116 in the direction facing the tibia 80 and opposite to the direction of the tibial flange 114, although in another aspect generally referenced at 200 and illustrated in FIGS. 6-9, the tibial dome 212 does not rise above the tibial plate 216 defining instead a pocket, also referenced as 212, in the tibial component 210. The tibial dome/pocket 112/212 presents a concave articulating surface 126/226 in the direction facing the talus 82. The tibial dome/pocket 112/212 can be a portion of a sphere having a radius r, although other shapes are contemplated, such as a portion of a cone, a portion of a cylinder, etc.

Figure 6:
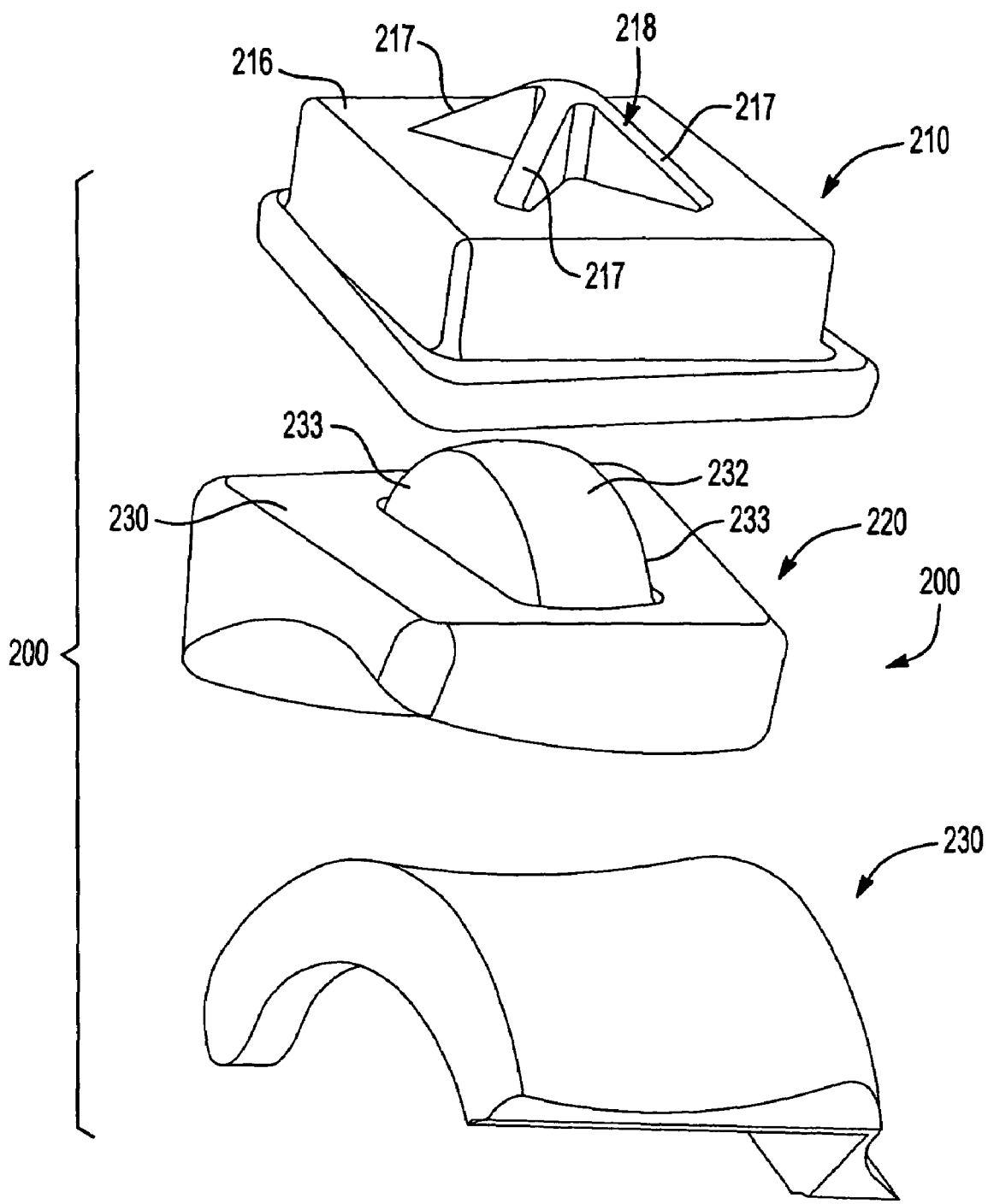
FIG. 6 is an exploded isometric view of an ankle implant according to the present teachings.
Figure 7:
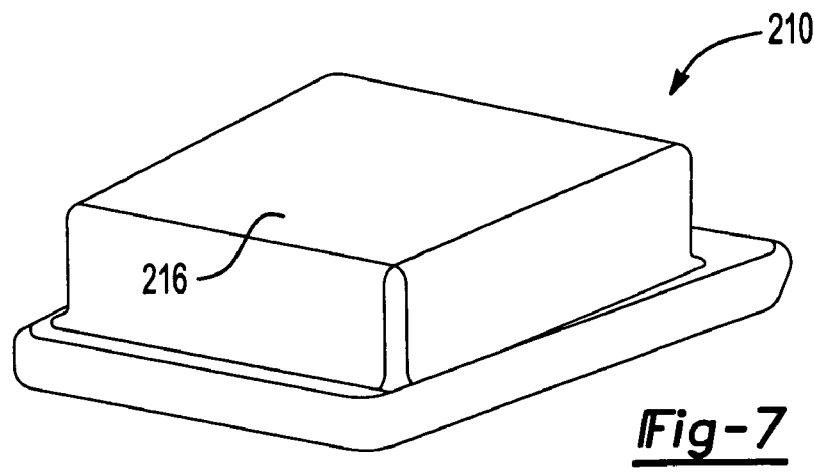
FIG. 7 is a top isometric view of a tibial component according to the present teachings.
Figure 8:
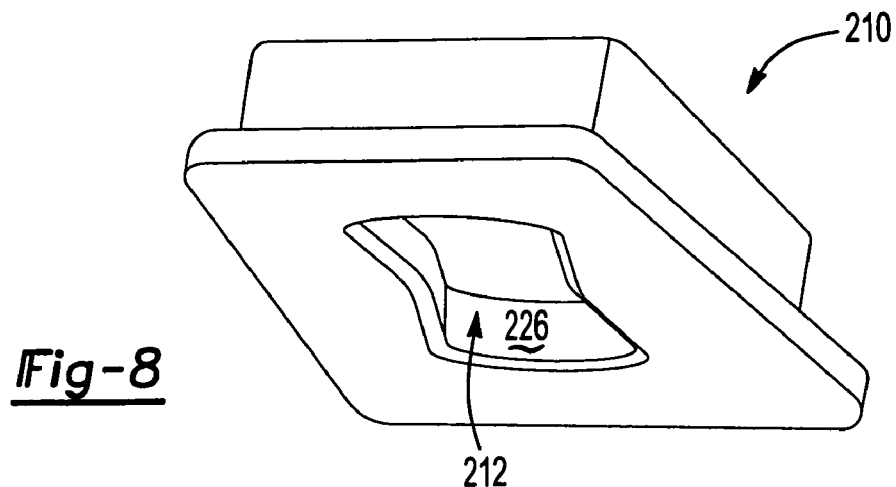
FIG. 8 is a bottom isometric view of the tibial component of FIG. 7.

In various aspects, a plurality of radially extending ribs 117/217 can be attached to the convex surface 124, as shown in FIG. 1, or can rise above a flat tibial plate 216, as shown in FIG. 6, defining a rib structure or cage 118/218. The rib structure 118 protects the integrity of the tibial dome 112 and provides anchoring to pressure-fit the tibial component 110/210 into the tibia 80. Posts 122 extending from the tibial plate 116 in the direction facing the tibia 80 can also be provided for additional anchoring stability. The posts 122 can be of cylindrical, conical, tooth-like, barbed or other shape suitable for anchoring. The post 122 can be attached to the tibial plate 116 at the terminating ends 119 of the ribs 117, or elsewhere. As illustrated in FIGS. 6 and 7, the cage 118 and or/the posts 122 can be entirely omitted from the tibial component 210.

Referring to FIG. 1, the bearing 120 includes a bearing plate 136 and a bearing flange 138 that extends from a side 131 of the bearing plate 136 such that the bearing plate 136 and the bearing flange 138 define an a profile that can mate with the L-profile of the tibial component 110. The bearing plate 136 defines a circumference 133 capped by a bearing dome 132. The bearing dome 132 has a convex bearing surface 134 rising above the bearing plate 136 in the direction facing the concave bearing surface 126 of the tibial dome 112 and opposite to the direction of the bearing flange 138. The concave surface 126 of the tibial dome 112 is sized to conform and rotatably articulate with the convex surface 134 of the bearing dome 132 for rotation (abduction and adduction) in the transverse plane in the direction of arrows "A". The arrangement of the tibial and bearing flanges 114, 138 is designed to limit the degree of relative rotation to a desired range, such as, for example, to a range of about 5°-10°, to replicate the motion of the natural ankle joint, although other ranges are also contemplated herein. The tibial and bearing flanges 114, 138 have mutually engaging surfaces 113, 115 that can be planar or curved.

Although the tibial dome 112 and the bearing dome 132 are shown as being convex in the direction facing the tibia 80, inverted domes are also contemplated herein, such that both the tibial dome 112 and the bearing dome 132 have concave faces directed toward the tibia 80. The domes 112, 132 can be portions of hemispheres or have other curved shapes that allow relative rotation or other articulation therebetween, such as, for example, portions of paraboloids, ellipsoids, cones, cylinders, etc.

Figure 2:
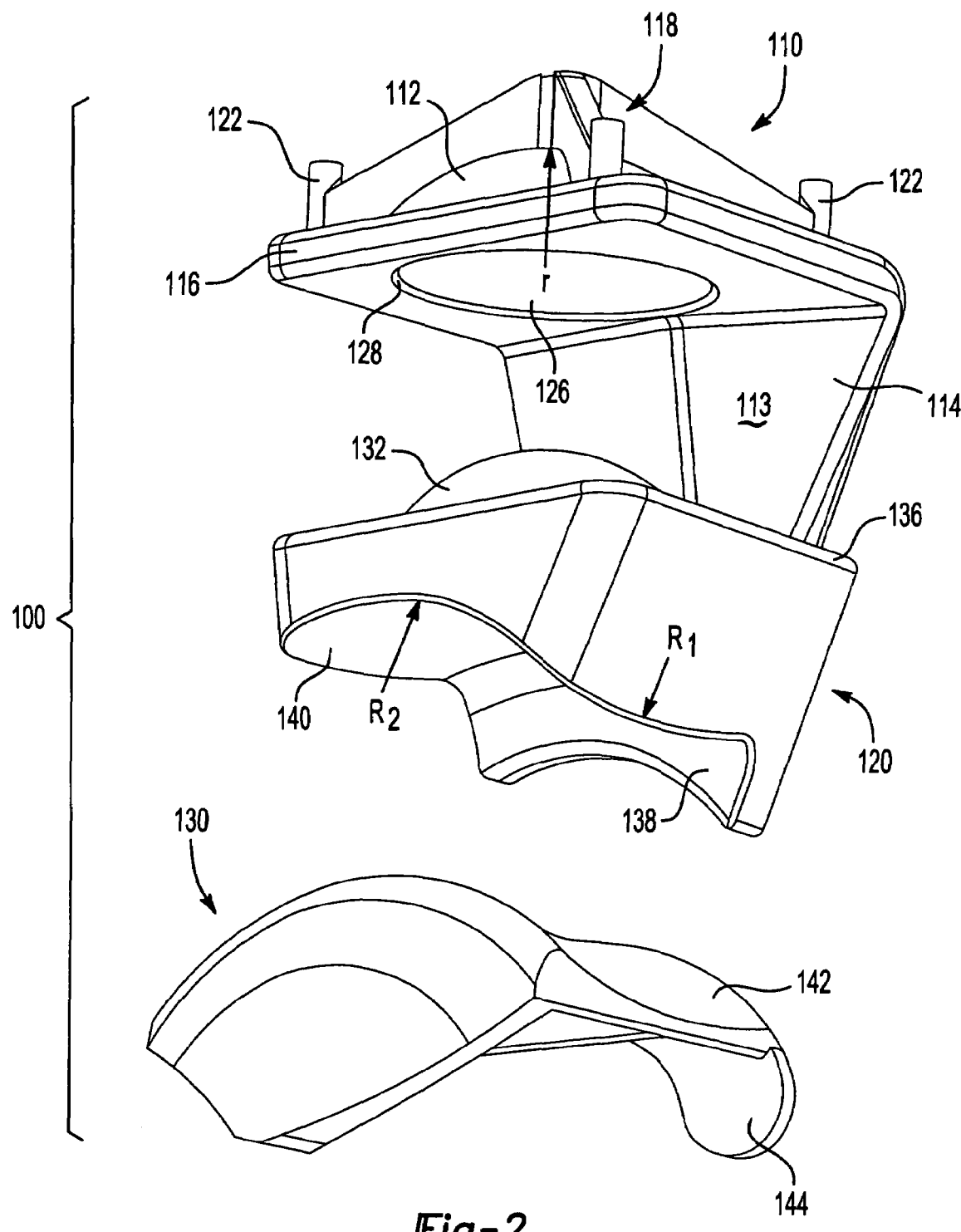
Figure 3:
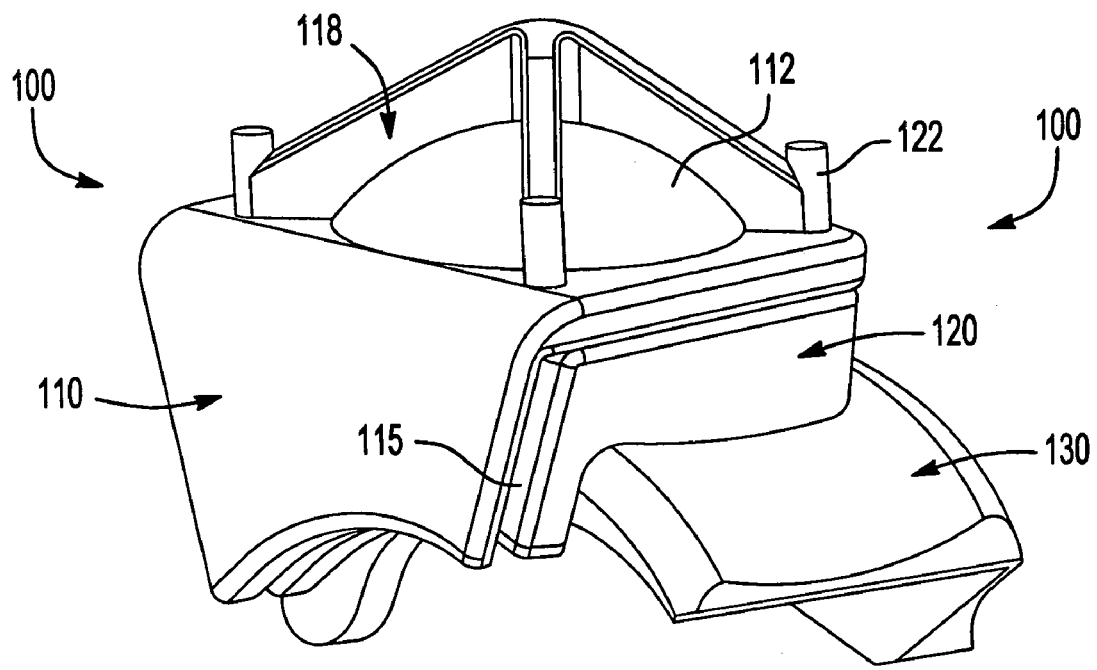
FIGS. 3 and 4 are top isometric views of an assembled ankle implant according to the present teachings.
Figure 4:
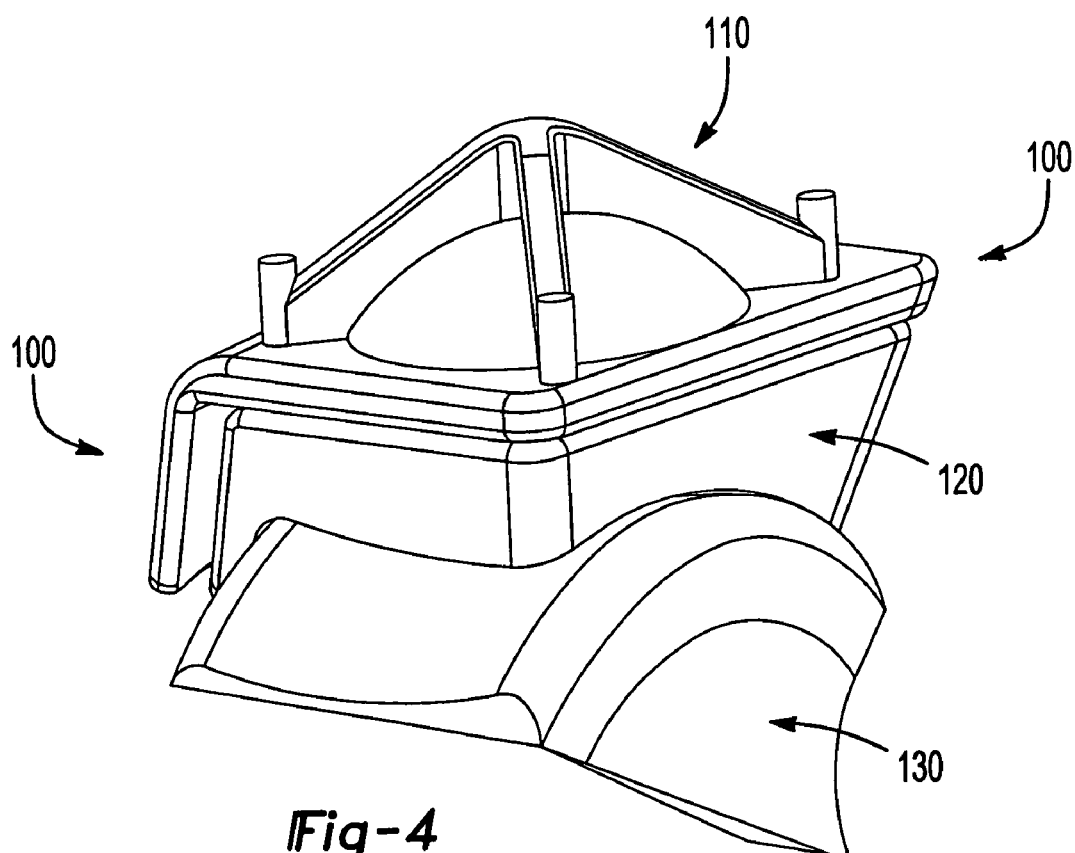

Referring to FIG. 2, the bearing 120 has a lower arcuate bearing surface 140 that is facing the talar component 130 and is on the opposite side of the bearing dome 132. The lower surface 140 of the bearing 120 conforms and articulates with an upper surface 142 of the talar component 130. The articulating bearing and talar surfaces 140, 142 are doubly-curved surfaces having two radii of curvature $R_1$ and $R_2$ in planes that are at an angle to each other, such as, for example, mutually perpendicular planes. This articulation is of the "hinged" type and permits motion in the sagittal plane in dorsiflexion and plantarflexion in the direction of arrows "B", and motion in the coronal plane, eversion and inversion, in the direction of arrows "C".

Figure 5:
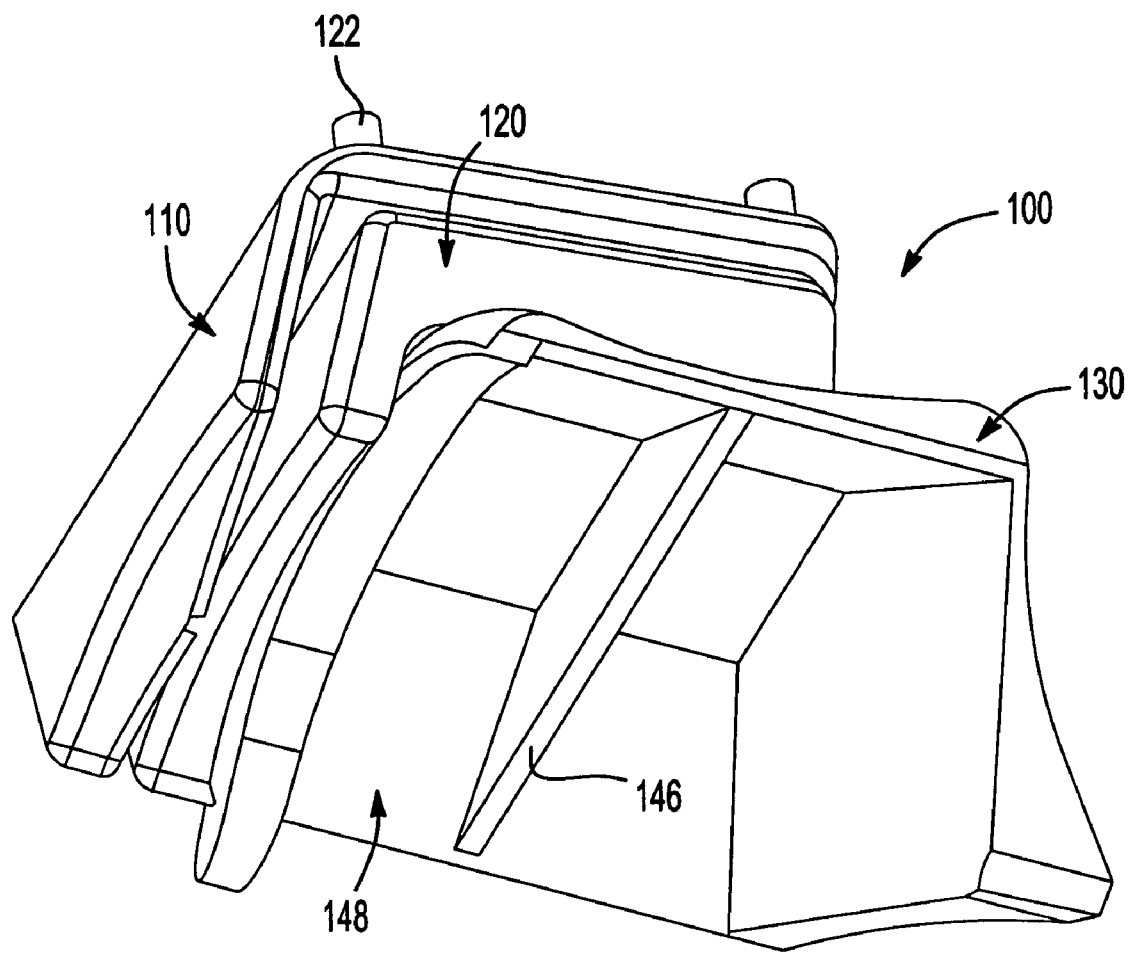
FIG. 5 is a bottom isometric view of an assembled implant according to the present teachings.

With reference to FIG. 5, the underside surface 148 of the talar component 130 has a trapezoidal profile and includes ridges, such as a median ridge 146 for snap-on attachment with a prepared talus 82. An end flange 144 can also be used for attachment to the talus 82.

Figure 9:
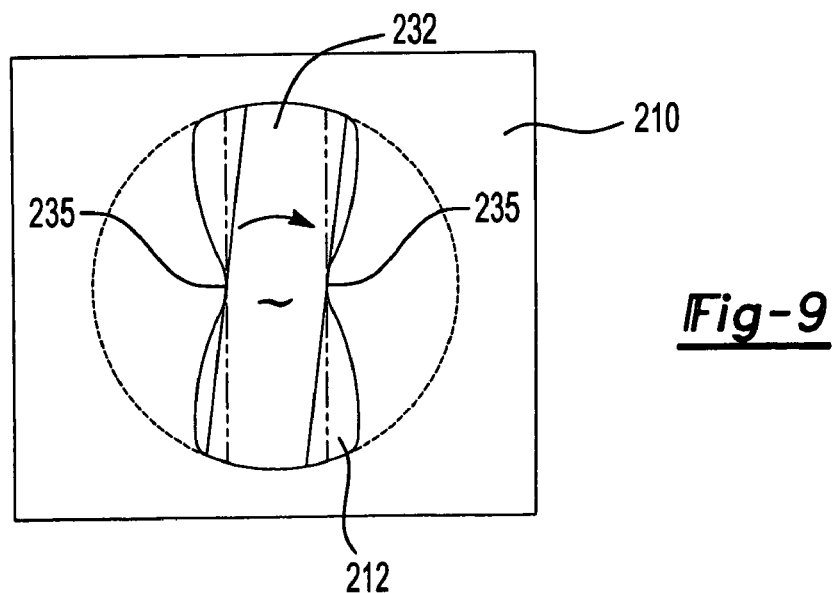
FIG. 9 is a bottom view of a tibial component illustrating constrained rotation of a bearing dome according to the present teachings.

Referring to FIGS. 6-9, other aspects of the ankle implant, generally referenced at 200, are illustrated. According to these aspects, the tibial component 210 and the bearing 220 do not include flanges to achieve semi-constrained motion, relying instead on the geometry of the concave surface 226 of the talar dome 212 which forms a pocket, and the geometry of a bearing dome 232 that rises above a bearing plate 236. The bearing dome 232, can be, for example, a portion of a sphere between two parallel planes 233. The bearing dome 232 is received in the concave surface 226 of the talar dome/pocket 212, which includes protrusions 235 to allow limited rotation of the bearing dome 232 relative to the tibial component 210 in the transverse plane, as shown in FIG. 9.

It will be appreciated that the semi-constrained design of the present teachings provides stability by limiting rotation in the transverse plane in emulation of the natural ankle joint, while offering articulation that allows desirable motion in the sagittal and coronal planes.

In use, after the tibia 80 and the talus 82 have been exposed, the tibia 80 is prepared to receive the tibial component 110. Likewise, the talus 82 is prepared to receive the talar component 130. The tibial component 110 and the talar component 130 are implanted and articulated with the bearing 120. The implantation is completed by additional anchoring and/or suturing.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A modular ankle implant comprising:
    a tibial component having a tibial dome and a single tibial flange;
    a talar component; and
    a bearing matingly articulating with the talar component, the bearing having a bearing dome mating with the tibial dome for relative rotation therebetween, and a single bearing flange engaging the tibial flange to limit rotation of the bearing relative to the tibial component.

2. The ankle implant of claim 1, wherein the bearing and the talar component articulate over a doubly-curved surface for relative movement therebetween.

3. The ankle implant of claim 2, wherein the doubly-curved surface has curvatures in two mutually perpendicular planes.

4. The ankle implant of claim 1, wherein the tibial and bearing domes are selected from the group consisting of sphere, cylinder, cone and portions thereof.

5. The ankle implant of claim 1, wherein the tibial component includes a rib structure over a convex surface of the tibial dome for securing the tibial component to bone.

6. The ankle implant of claim 1, wherein the bearing dome has a convex surface articulating with a concave surface of the tibial dome.

7. The ankle implant of claim 1, wherein the single tibial flange is only one tibial flange extending from only one side of the tibial component, and the single bearing flange is only one bearing flange extending from only one side of the bearing component.

8. A modular ankle implant for implantation between a tibia and a talus, the implant comprising:
    a tibial component having an annular plate, a tibial dome and a only one tibial flange, wherein the dome has convex and concave surfaces that are bounded by the annular plate, and wherein the tibial flange extends from only one side of the annular plate at an angle relative to the annular plate;
    a talar component having a doubly-curved surface; and
    a bearing having a bottom surface, a bearing dome and only one bearing flange, wherein the bottom surface matingly articulates with the doubly-curved surface of the talar component for hinged movement therebetween, the bearing dome has a convex surface mating with the concave surface of the tibial dome for relative rotation therebetween, and the bearing flange interacts with the tibial flange to limit rotation of the bearing relative to the tibial component.

9. The ankle implant of claim 8, wherein the tibial and bearing domes are selected from the group consisting of sphere, cylinder, cone and portions thereof.

10. The ankle implant of claim 8, wherein the tibial component includes a rib structure over the convex surface of the tibial dome for implantation into a tibia.

11. The ankle implant of claim 8, wherein the tibial component includes posts extending from the plate for implantation into the tibia.

12. The ankle implant of claim 8, wherein the talar component has a ridged structure for implantation into the talus.

13. The ankle implant of claim 8, wherein the doubly-curved surface has curvatures in two mutually perpendicular planes.

14. A modular ankle implant comprising:
a tibial component coupled to a talar component with a bearing, wherein the bearing is adapted for hinged articulation relative to the talar component and limited rotation relative to the tibial component, and wherein rotation between the bearing and the tibial component is effected by engagement of conforming domes extending respectively from the bearing and the tibial component, the tibial component including radial ribs extending from the dome of the tibial component, and posts for tibial anchoring, wherein the posts are at the ends of the radial ribs.

15. The ankle implant of claim 14, wherein hinged articulation includes flexion in a sagittal plane and rotation in a coronal plane.

16. The ankle implant of claim 14, wherein limited rotation relative to the tibial component includes rotation in a transverse plane.

17. The ankle implant of claim 16, wherein limited rotation includes a range of about 5° to 10°.

18. The ankle implant of claim 14, wherein rotation between the bearing and the tibial component is limited by engagement of a single bearing flange and a single tibial flange, the bearing and tibial flanges being parallel and extending respectively from the bearing and the tibial component.

19. The ankle implant of claim 14, wherein hinged articulation includes articulation between conforming doubly-curved surfaces of the bearing and the talar component.

20. A method for implanting an ankle joint prosthesis between a tibia and a talus, the method comprising:
attaching a tibial component to the tibia, the tibial component including only one tibial flange;
attaching a talar component to the talus;
articulating a bearing for rotation relative to the tibial component and hinged movement relative to the talar component; the bearing including only one bearing flange; and
limiting relative rotation between the tibial component and the bearing by engaging the tibial and bearing flanges.

21. The method of claim 20, wherein hinged movement includes movement between two conforming doubly curved surfaces of the bearing and the talar component.

22. The method of claim 20, wherein rotation is effected by engagement of conforming domes extending respectively from the bearing and the tibial component.

23. A modular ankle implant for implantation between a tibia and a talus, the implant comprising:
a tibial component including an inner pocket defining by a concave articulating surface and first and second sides including opposing curved protrusions extending into the pocket;
a bearing component including a bearing plate and a dome rising from the bearing plate, the dome received in the inner pocket of the tibial component, the dome including a convex articulating surface mating with the concave articulating surface of the inner pocket for relative rotation therebetween and two planar surfaces extending on opposite sides of the curved surface, the planar surfaces interacting with the curved protrusions limiting rotation of the bearing component relative to the tibial component; and
a talar component articulating with the bearing component for relative movement in sagittal and coronal planes.

24. The ankle implant of claim 23, wherein the convex and concave articulating surfaces are selected from the group consisting of sphere, cylinder, cone and portions thereof.

* * * * *